US008823790B2

(12) United States Patent
Dunn et al.

(10) Patent No.: US 8,823,790 B2
(45) Date of Patent: Sep. 2, 2014

(54) METHODS OF PRODUCING LASER SPECKLE CONTRAST IMAGES

(75) Inventors: Andrew Dunn, Austin, TX (US); William James Tom, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 541 days.

(21) Appl. No.: 13/211,956

(22) Filed: Aug. 17, 2011

(65) Prior Publication Data

US 2012/0071769 A1 Mar. 22, 2012

Related U.S. Application Data

(63) Continuation-in-part of application No. PCT/US2010/024435, filed on Feb. 17, 2010.

(60) Provisional application No. 61/153,006, filed on Feb. 17, 2009.

(51) Int. Cl.
*A61B 5/026* (2006.01)
*A61B 5/02* (2006.01)
*A61B 5/00* (2006.01)
*G02B 27/48* (2006.01)

(52) U.S. Cl.
CPC ............ *G02B 27/48* (2013.01); *A61B 5/02028* (2013.01); *A61B 5/0059* (2013.01); *A61B 5/7257* (2013.01); *A61B 5/0261* (2013.01)
USPC ............................................ 348/77; 382/128

(58) Field of Classification Search
CPC ............ A61B 5/0059; A61B 5/02028; A61B 5/0261; A61B 5/7257; G02B 27/48

USPC ................................. 348/77; 382/128; 600/504
See application file for complete search history.

(56) References Cited

U.S. PATENT DOCUMENTS

| 6,944,494 | B2 * | 9/2005 | Forrester et al. ............... 600/478 |
|---|---|---|---|
| 7,113,817 | B1 * | 9/2006 | Winchester et al. ........... 600/476 |
| 7,872,760 | B2 * | 1/2011 | Ertl ............................... 356/479 |
| 8,085,467 | B1 * | 12/2011 | Silverstein et al. ............ 359/443 |
| 8,509,879 | B2 * | 8/2013 | Durkin et al. .................. 600/473 |
| 2002/0016533 | A1 | 2/2002 | Marchitto et al. |
| 2008/0262359 | A1 | 10/2008 | Tearney et al. |
| 2011/0013002 | A1 * | 1/2011 | Thompson et al. .............. 348/77 |
| 2012/0095354 | A1 * | 4/2012 | Dunn et al. .................... 600/504 |

FOREIGN PATENT DOCUMENTS

WO 2009008745 A2 1/2009

OTHER PUBLICATIONS

International Search Report and Written Opinion for International Application No. PCT/US 2010/24435, dated Apr. 27, 2010.
International Preliminary Report on Patentability International Application No. PCT/US 2010/24435, dated Aug. 23, 2011.

* cited by examiner

*Primary Examiner* — Christopher S Kelley
*Assistant Examiner* — Asmamaw G Tarko
(74) *Attorney, Agent, or Firm* — Reed Smith LLP; Robert R. Riddle

(57) ABSTRACT

Methods of imaging are provided. In some embodiments, the methods may comprise obtaining a raw speckle image of a sample, converting the raw speckle image to a laser speckle contrast image using a laser speckle contrast algorithm, and converting a laser speckle contrast image to a relative correlation time image using a relative correlation time algorithm.

8 Claims, 8 Drawing Sheets

METHODS OF PRODUCING LASER SPECKLE CONTRAST IMAGES

CROSS-REFERENCE TO RELATED APPLICATIONS

This application is a continuation-in-part of PCT/US2010/24435 filed Feb. 17, 2010 and claims priority to U.S. Patent. App. Ser. No. 61/153,006 filed Feb. 17, 2009, which is incorporated herein by reference.

STATEMENT OF GOVERNMENT INTEREST

This invention was made with government support under Grant Number NS050150 awarded by the National Institutes of Health. The government has certain rights in the invention.

BACKGROUND

As blood flow is one of the most important physiological indicators, methods for dynamic monitoring of blood flow are of great interest in a wide range of applications and diseases. Optical techniques based on dynamic light scattering comprise a large number of the available methods for blood flow monitoring such as laser Doppler, speckle contrast imaging, and photon correlation spectroscopy. Although all these techniques differ in their measurement geometry and analysis, each is based on dynamic light scattering. Laser Doppler flowmetry is a well-established technique for measuring blood flow, although it is usually limited to measurements at single spatial locations. More recently, laser speckle contrast imaging (LSCI) has become widely used to image blood flow in a variety of tissues. Because LSCI enables full-field imaging of surface blood flow using simple instrumentation, it has distinct advantages over techniques such as laser Doppler flowmetry. Although the instrumentation for LSCI is simple, obtaining quantitative measures of blood flow can be challenging due to the complex physics that relate the measured quantities to the underlying blood flow.

The advantages of LSCI have created considerable interest in its application to the study of blood perfusion in tissues such as the retina and the cerebral cortices. In particular, functional activation and spreading depolarizations in the cerebral cortices have been explored using LSCI. The high spatial and temporal resolution capabilities of LSCI are incredibly useful for the study of surface perfusion in the cerebral cortices because perfusion varies between small regions of space and over short intervals of time.

One criticism of LSCI is that images are produced slower than real-time. Due to the limited time available during biomedical imaging procedures, it is essential to increase the speed by which the images are produced. Delayed image production is a serious problem, leading to incomplete measurements and improper diagnoses. Regrettably, the processing of laser speckle contrast images has previously required about a second to process a frame while acquisition can occur at rates exceeding 100 frames per second. Consequently, the processing speed of laser speckle contrast images hinders complete use of the available temporal resolution.

SUMMARY

The present disclosure generally relates to methods of imaging blood flow, and more specifically, to methods of producing laser speckle contrast images and relative correlation time images.

In some embodiments, the present disclosure provides methods comprising obtaining a raw speckle image of a sample; converting the raw speckle image to a laser speckle contrast image using a laser speckle contrast algorithm; and converting a laser speckle contrast image to a relative correlation time image using a relative correlation time algorithm. In some embodiments, the laser speckle contrast algorithm may be a direct algorithm, a sums algorithm, a FFT algorithm, a roll algorithm, a vectorized algorithm, and a threaded algorithm. In some embodiments, the relative correlation time algorithm may be a "Newton" method algorithm, a "table" method algorithm, a "hybrid" method algorithm, and an "asymptote" method algorithm.

The methods of the present disclosure may be implemented in software to run on one or more computers, where each computer includes one or more processors, a memory, and may include further data storage, one or more input devices, one or more output devices, and one or more networking devices. The software includes executable instructions stored on a tangible medium.

DRAWINGS

Some specific example embodiments of the disclosure may be understood by referring, in part, to the following description and the accompanying drawings.

Figure 4A:
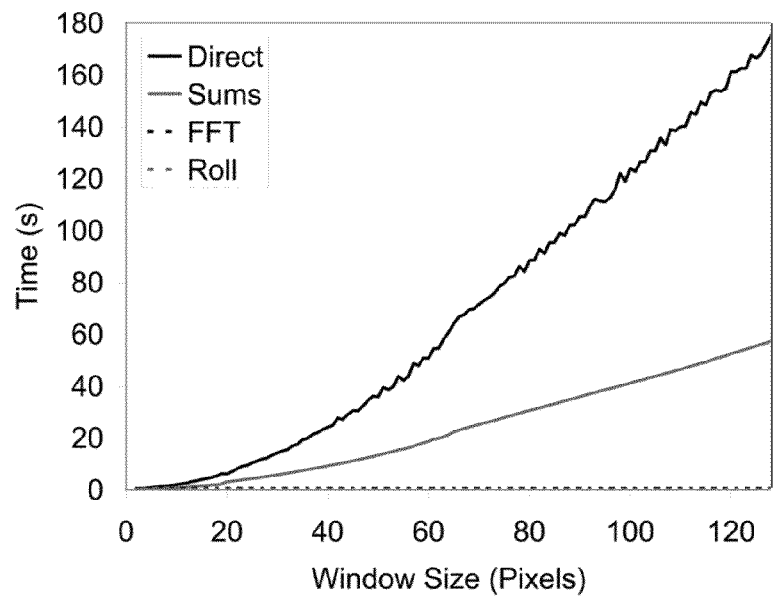

FIG. 4A is a graph depicting the average time in seconds to process 10 raw images with dimensions of 768×512 as the square window is varied from 2×2 to 128×128 pixels. Each measurement was repeated 10 times. The standard error of the mean was always less than 161, 72, 0.91, and 0.15 ms for the direct, sums, FFT, and roll algorithms, respectively.

Figure 4B:
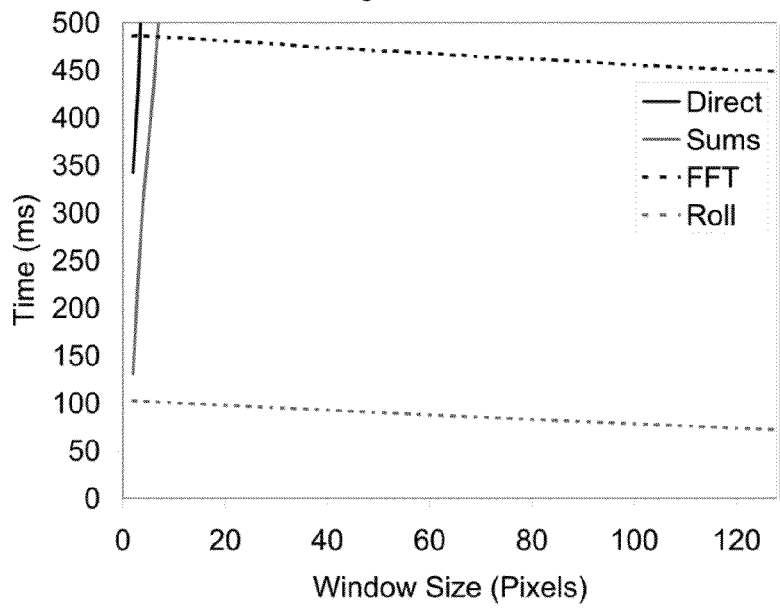

FIG. 4B is a magnified version of FIG. 4A in milliseconds instead of seconds. Each measurement was repeated 10 times. The standard error of the mean was always less than 161, 72, 0.91, and 0.15 ms for the direct, sums, FFT, and roll algorithms, respectively.

Figure 5A:
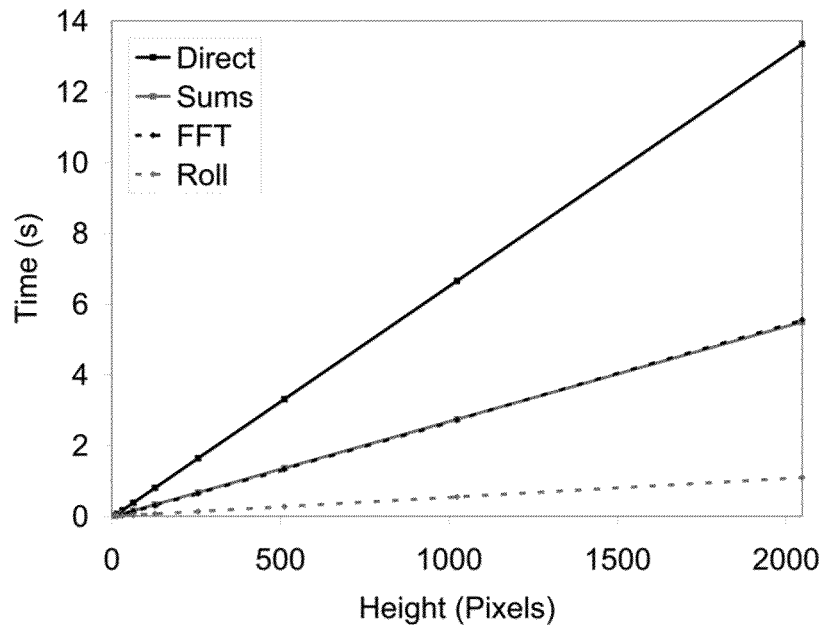

FIG. 5A is a graph depicting the average time in seconds to process 10 raw images 2048 pixels wide with a window size of 7×7 pixels as height is incremented from 2 to 2048 pixels by powers of 2. The sums and FFT performance curves overlap. Each measurement was repeated 10 times, and the standard error of the mean was always less than 12.2 ms.

Figure 5B:
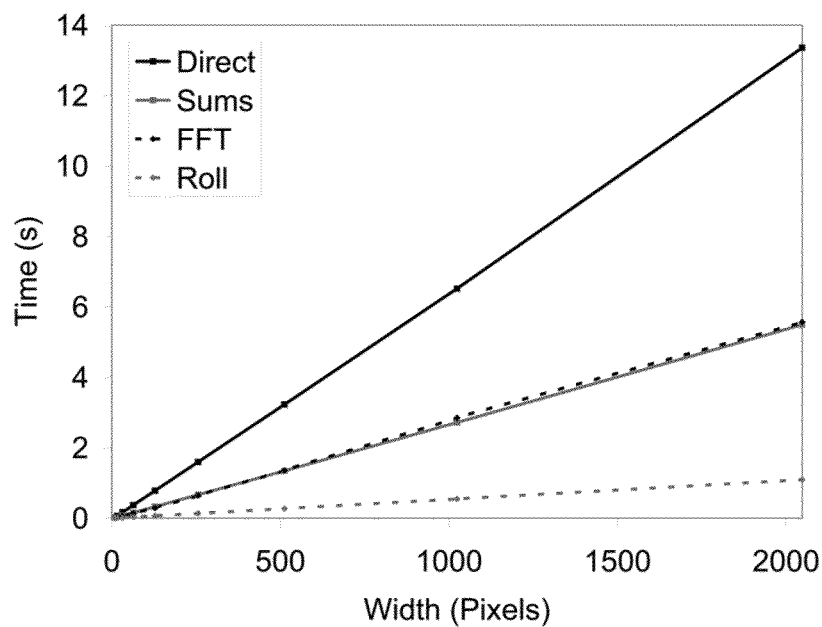

FIG. 5B is a graph depicting the average time in seconds to process 10 raw images 2048 pixels high with a window size of 7×7 pixels as width is incremented from 2 to 2048 pixels by powers of 2. The sums and FFT performance curves overlap.

Each measurement was repeated 10 times, and the standard error of the mean was always less than 12.2 ms.

Figure 6:
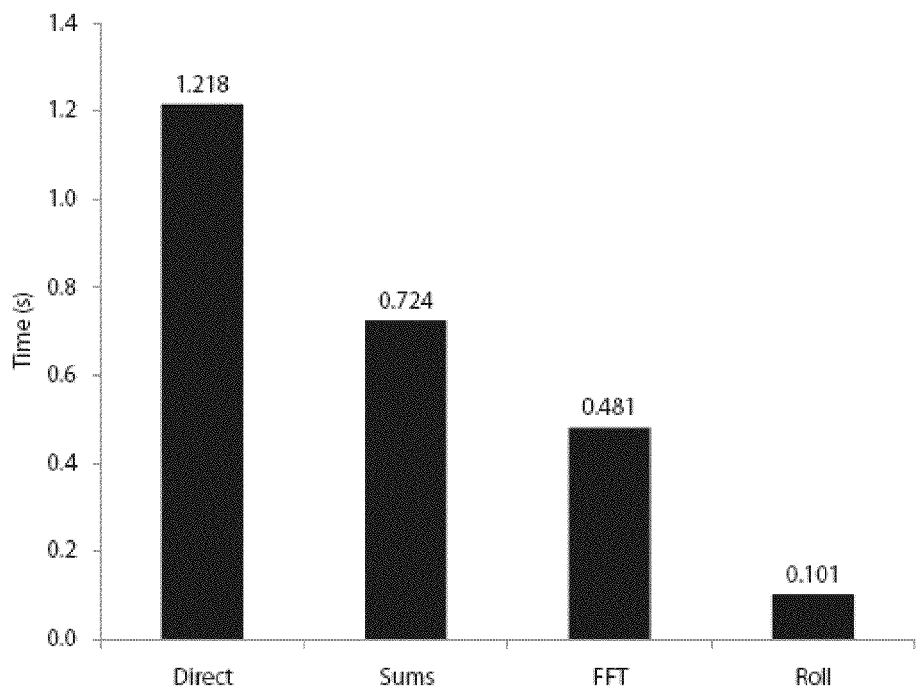

FIG. 6 is a graph representing the average computation times in seconds of laser speckle contrast algorithms with 10 raw images sized 768×512 and a window size of 7×7 pixels which represents typical experimental conditions. Each measurement was repeated 100 times, and the standard error of the mean was always less than 1.1 ms.

Figure 7:
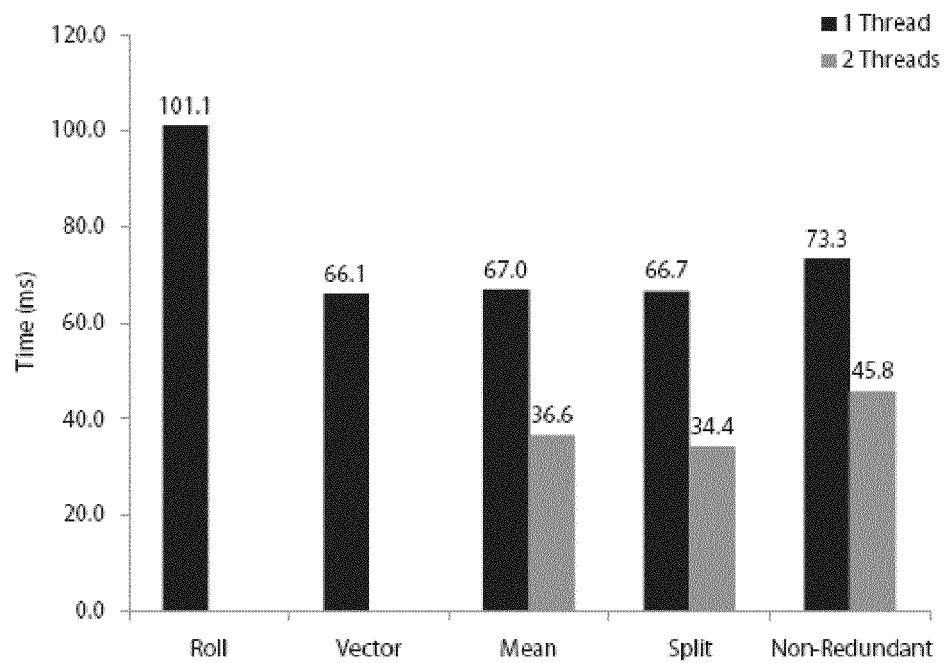

FIG. 7 is a graph representing the average computation times in milliseconds of vectorized and threaded laser speckle contrast algorithms with 10 raw images sized 768×512 and a window size of 7×7 pixels which represents typical experimental conditions. The split multithreaded algorithm yields the fastest computation time of 34.4 ms which is equivalent to 291 frames per second. Each measurement was repeated 100 times, and the standard error of the mean was always less than 0.10 ms.

Figure 8:
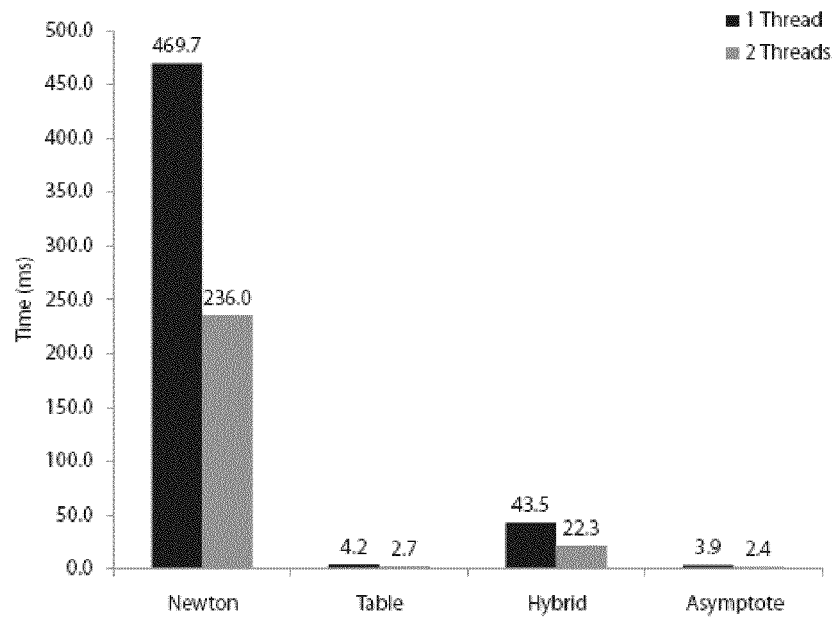

FIG. 8 is a graph representing the average computation times in milliseconds of relative correlation time algorithms with a laser speckle contrast image sized 762×506 which represents typical experimental conditions. Each measurement was repeated 100 times. For the Newton algorithm, the standard error of the mean was always less than 0.14 ms, while the standard error of mean was always less than 0.04 ms for the other algorithms.

Figure 9:
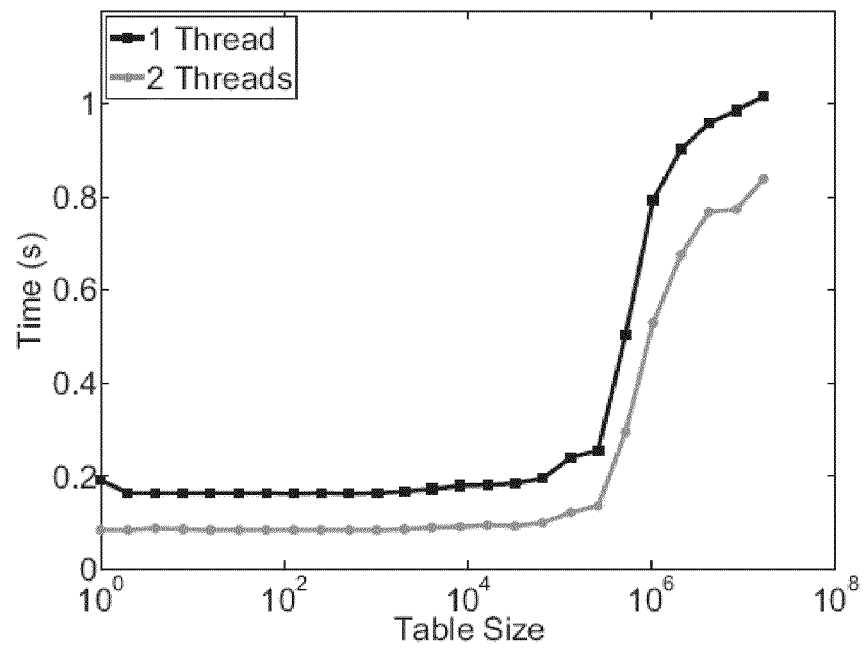

FIG. 9 graphs the average computation time in seconds of the table method with a laser speckle contrast image sized 4096×4096 as table size is varied. Each measurement was repeated 100 times, and the standard error of the mean was always less than 0.33 ms.

Figure 10:
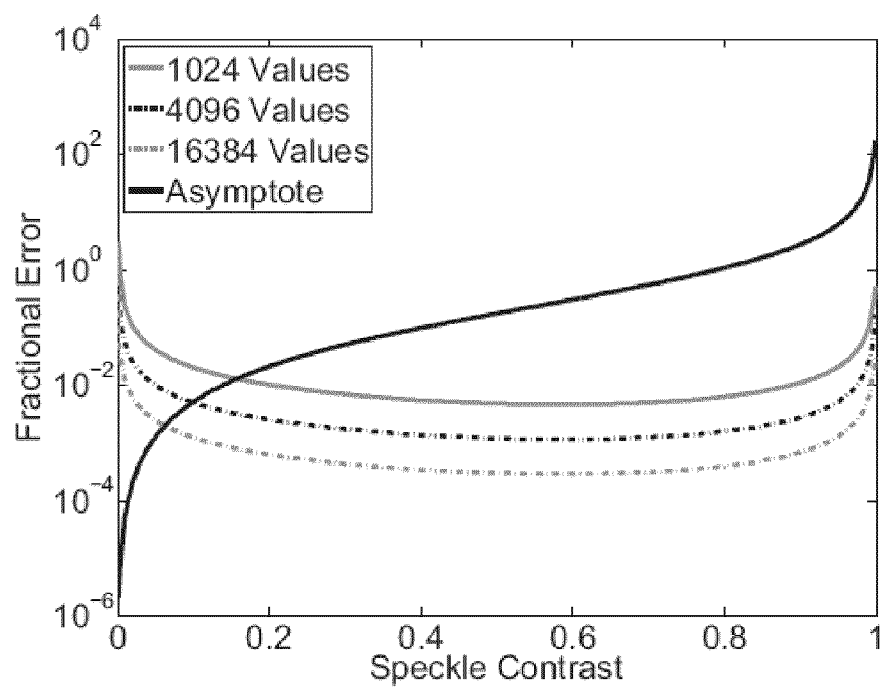

FIG. 10 graphs the fractional error in determining the ratio of exposure duration to correlation time by the table and asymptote methods as speckle contrast is varied. The curves labeled "1024 Values," "4096 Values," and "16384 Values" represent the maximum fractional error for the table method with a table size of 1024, 4096, and 16384 values, respectively.

The patent or application file contains at least one drawing executed in color. Copies of this patent or patent application publication with color drawing(s) will be provided by the Office upon request and payment of the necessary fee.

While the present disclosure is susceptible to various modifications and alternative forms, specific example embodiments have been shown in the figures and are described in more detail below. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to methods of imaging blood flow, and more specifically, to methods of producing laser speckle contrast images and relative correlation time images.

Laser Speckle Contrast Imaging (LSCI) is an optical technique useful for the characterization of scattering particle dynamics with high spatial and temporal resolution. In some embodiments, LSCI can be used to generate an image depicting blood flow of biological tissues in vivo with high spatial and temporal resolution. Unfortunately, the usefulness of LSCI has been previously limited because image processing was slow. The present disclosure provides methods for processing raw speckle images to convert them to laser speckle contrast images and for converting laser speckle contrast images to relative correlation time images using algorithms that render processing time nearly irrelevant in most circumstances and enable real-time imaging of blood flow dynamics. The methods of the present disclosure provide a dramatic improvement in processing times without any approximations.

In some embodiments, the methods of present disclosure allow processing of laser speckle contrast images at orders of magnitude greater speed than currently used algorithms. The methods of the present disclosure generally comprise obtaining a raw speckle image of a sample; converting the raw speckle image to a laser speckle contrast image using a laser speckle contrast algorithm; and converting a laser speckle contrast image to a relative correlation time image using a relative correlation time algorithm. Examples of suitable laser speckle contrast algorithms include, but are not limited to, a direct algorithm, a direct algorithm using sums ("sums algorithm"), a fast Fourier transform-based convolution algorithm ("FFT algorithm"), a roll algorithm, a vectorized algorithm ("vector"), and threaded algorithms, including, but not limited to, a "mean" threading algorithm, the "split" method algorithm, and the "non-redundant" method algorithm. Similarly, examples of suitable relative correlation time algorithms include, but are not limited to, the "Newton" method algorithm, the "table" method algorithm, the "hybrid" method algorithm, and the "asymptote" method algorithm. Each of these algorithms will be discussed in more detail below.

In general, speckle arises from the random interference of coherent light. When collecting laser speckle contrast images, coherent light is used to illuminate a sample and a photodetector is then used to receive light that has scattered from varying positions within the sample. The light will have traveled a distribution of distances, resulting in constructive and destructive interference that varies with the arrangement of the scattering particles with respect to the photodetector. When this scattered light is imaged onto a camera, it produces a randomly varying intensity pattern known as speckle. If scattering particles are moving, this will cause fluctuations in the interference, which will appear as intensity variations at the photodetector. The temporal and spatial statistics of this speckle pattern provide information about the motion of the Theoretically, the speckle contrast has a value between 0 and 1, provided that the speckle pattern is fully evolved. A speckle pattern is considered fully evolved provided that the phases of the interfering electromagnetic fields are uniformly distributed, as can be verified by confirming a negative exponential probability distribution of the speckle intensity pattern. A spatial speckle contrast of 1 indicates that there is no blurring of the speckle pattern and therefore, no motion, while a speckle contrast of 0 means that the scatterers are moving fast enough to blur all of the speckles. The speckle contrast is a function of the exposure time of the camera.

The speckle contrast is therefore a measure of the local spatial contrast in the speckle pattern. A spatially resolved map of local speckle contrast can be calculated from a raw speckle image by computing this ratio at each point in the image from the pixels over a region of an image, typically a square, which is hereinafter referred to as a "window." For purposes of this disclosure, the length of the side of a square window in pixels will be represented by w. The width and height of a raw image in pixels will be represented by m and n, respectively, while the width and height of a processed image are $m'=m-w+1$ and $n'=n-w+1$, respectively.

One of the reasons that LSCI has become a widely adopted method for imaging blood flow is the relative simplicity of the instrumentation. According to one embodiment, a basic configuration may comprise a coherent light source, such as a laser diode, whose beam is expanded and adjusted to illuminate the area of interest, which can vary from a few millimeters to several centimeters. The angle of the incident light may range from near normal incidence to as much as 45°. Additionally, a suitable configuration comprises a photodetector, such as a camera. Light scattered from a sample is imaged onto the camera to enable recording of the speckle pattern. The specifications of cameras suitable for use in the present disclosure vary widely, but inexpensive 8-bit cameras have been demonstrated to provide excellent images of blood flow and enable detailed physiological studies to be performed. In general, high dynamic range cooled cameras are not required for LSCI because the light levels reaching the camera are usually high enough that the majority of noise arises from shot noise. In addition, the speckle pattern is inherently high in contrast, so that 8-bit cameras have sufficient dynamic range to accurately quantify speckle contrast.

Figure 1A:
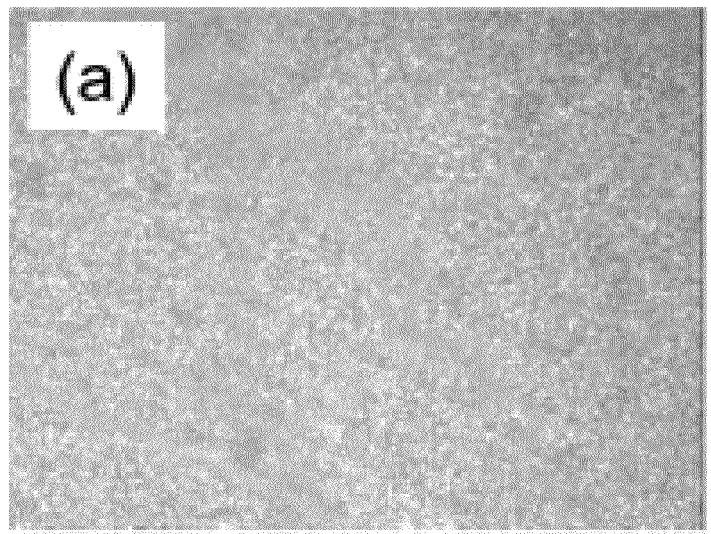
FIG. 1A depicts a raw speckle image from the thin skull of a rat, showing a grainy pattern in which it is possible to discern some spatial variation in the speckle contrast.
Figure 1B:
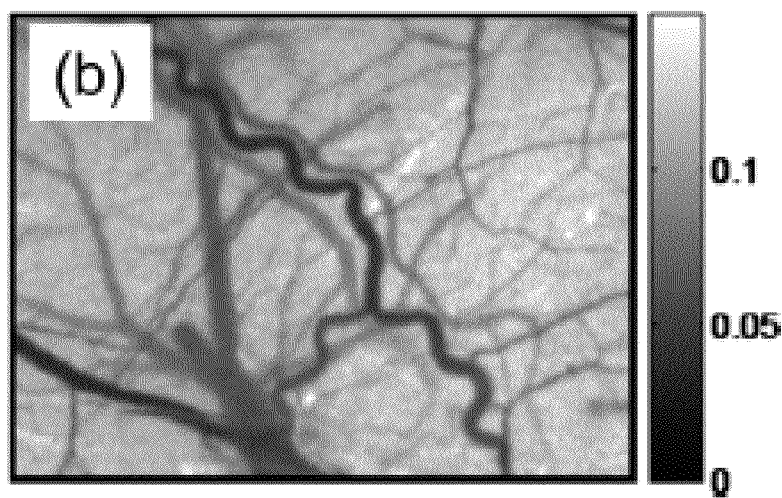
FIG. 1B depicts a spatial speckle contrast image estimated from a 7×7 window of pixels.

A typical example of a raw speckle image of the rat cortex, taken through a thinned skull, and the computed laser speckle contrast image are shown in FIG. 1 under normal conditions. The raw speckle image shown in FIG. A illustrates the grainy appearance of the speckle pattern. The laser speckle contrast image shown in FIG. 1B, computed directly from the raw speckle image using Equation 1, represents a 2-D map of blood flow. Areas of higher baseline flow, such as large vessels, have lower speckle contrast values and appear darker in the speckle contrast images.

A. Laser Speckle Contrast Algorithms

As mentioned above, the present disclosure provides several different laser speckle contrast algorithms for the computation of a laser speckle contrast image from a raw speckle image. In particular, the present disclosure provides a direct algorithm, a sums algorithm, a FFT algorithm, a roll algorithm, a vector method algorithm and threaded algorithms. A description of each algorithm is described below.

1. Direct Algorithm

In the direct algorithm, Equation 1 is repeatedly evaluated as the window is slid across the image. First, the mean of the time-integrated intensity values over the window is computed. Then the difference between each time-integrated intensity value of the window and the mean is squared and summed with the other squared differences. The final sum is divided by $w^2-1$, and the square root is evaluated. The final step is division by the mean.

For image generation, the window is moved horizontally and vertically while repeating the process described here. Ignoring the memory required for the raw images and the laser speckle contrast images, memory consumption is O(1) from Equation 1. In future discussion, as it has been here, the memory unavoidably consumed by the raw images and laser speckle contrast images will not be included in an algorithm's memory consumption to prevent obscuring algorithmic differences by such an inclusion.

In prior art, it is has been noted that processing a laser speckle contrast image using Equation 1 is relatively slow, requiring about 13 seconds per speckle contrast image including a minor portion of the time for additional processing. In other art, 7.5 seconds were required to generate a laser speckle contrast image from 10 raw frames with collection occurring at 150 frames per second. Clearly, the processing is much slower than the rate at which images are acquired.

2. Sums Algorithm

A modification of the direct algorithm is to express the standard deviation in an alternate form with sums as in Equation 2.

$$k = \frac{s_I}{\langle I \rangle} = \frac{\sqrt{\frac{N \sum_{i=1}^{N} I_i^2 - \left(\sum_{i=1}^{N} I_i\right)^2}{N(N-1)}}}{\frac{\sum_{i=1}^{N} I_i}{N}} \quad (2)$$

First, the sum of all of the time-integrated intensity values within the window is calculated, followed by the sum of all of the squared time-integrated intensity values within the window. Then the sum of the squares is multiplied by $w^2$, and the sum squared is subtracted. The difference is divided by $w^2(w^2-1)$. After determining the square root, the result is divided by the mean. Note that the sums and the sums of squares of the time-integrated intensities quantized by the camera should be computed exactly using integer arithmetic to avoid low computational precision associated with Equation 2 and finite precision arithmetic when the speckle contrast is small. Like the direct algorithm, memory consumption is O(1) as in Equation 1.

3. FFT Algorithm

By considering the problem as a computation involving sums and sums of squares, more efficient methods may be derived which achieve greater efficiency by optimizing calculation of the sums and sums of squares. In fact, there are a considerable number of computations which are wasted whenever the sum, sum of the squares, and the mean is reinitialized when translating the window. One method to exploit the calculations from neighboring windows is to compute the sums and sums of the squares as a convolution with a square window with constant coefficients. The convolution may be performed in the frequency domain with a FFT. First the FFT of the window is computed. The result may be computed before processing a batch of images with the same window and image size. Next, the FFT of the image is complex multiplied by the FFT of the window element-by-element to achieve convolution. An inverse FFT yields an image which consists of the sums. The same process is performed on an image in which its elements have been squared. Computation of the speckle contrast values occurs via the same final steps as the sums method. Since using an FFT necessitates floating-point arithmetic for the sums and sums of squares, high precision floating-point arithmetic may be necessary to avoid computational inaccuracy. Unlike the direct and sums method which require only stack space, in addition to stack space the FFT method requires two 2-D arrays of complex numbers and two 2-D arrays of real numbers all with dimensions equal to the dimensions of the raw image. Hence, the FFT method consumes $O_{mn}$ memory.

4. Roll Algorithm

Although the FFT is an efficient algorithm, exploitation of the nature of the speckle contrast computation allows bypassing it for greater performance. Rather than perform convolution, vertical and horizontal rolling sums are computed for the image and a squared version of the image. For discussion, the vertical rolling sums will proceed from the top to the bottom of the image, while the horizontal rolling sums will be from the left to the right. First, the top w rows are summed as vectors to initialize the row of accumulated sums (Step 1). Then, the subsequent rows below are processed iteratively one at a time from the top to the bottom by vector subtraction of the row which is w rows above from the row of accumulated sums immediately followed by vector addition of the current row. The row of accumulated sums is stored once for each row below the top w−1 rows to produce a 2-D array with dimensions m and n−w+1 (Step 2). All further operations are performed on the new 2-D array resulting from this vertical rolling sums process. Next, the leftmost w columns are added as vectors to initialize the column of accumulated sums (Step 3). Then for each remaining column, the column which is w columns to the left is subtracted vectorially from the column of accumulated sums followed by vector addition of the current column in an iterative manner completely analogous to the process applied to the rows except proceeding from left to right rather than top to bottom. For all columns to the right of the leftmost w−1 columns, the column of accumulated sums overwrites the columns of the 2-D array containing the vertical rolling sums one column at a time proceeding sequentially from the leftmost column to the m−w+1 column which is furthest on the right (Step 4). The final 2-D array with effective dimensions of m−w+1 and n−w+1 contains the sums of time-integrated intensity over each possible window. Squared sums may be calculated by first squaring the values and using the same process. Finalization of the computation proceeds in the same manner as the two previously discussed algorithms (Step 5). This algorithm is easily generalized to rectangular windows. As with the sums algorithm, exact integer arithmetic is used for computing the sums and sums of squares to avoid computational inaccuracy.

The pseudocode below implements the roll method as described above.

$$\vec{R_i}(\text{Image}) \quad \text{and} \quad \vec{C_j}(\text{Image})$$

and indicate the i th row vector of Image and the j th column vector of Image respectively. Operator symbols represent conventional vector operations. Raw, K, Sum, and SqSum are 2-D arrays or images which represent the raw image, the speckle contrast image, the sum image, and the square sum image, respectively, while $$\vec{\text{SumAc}} \quad \text{and} \quad \vec{\text{SqSumAc}}$$

are vector accumulators which hold the rolling sums and square sums, respectively. The parenthetical steps from the above description precede the pseudocode that implements the step. scattering particles. The motion can be quantified by measuring and analyzing temporal variations and/or spatial variations.

Using the latter approach, 2-D maps of blood flow can be obtained with very high spatial and temporal resolution by imaging the speckle pattern onto a camera and quantifying the spatial blurring of the speckle pattern that results from blood flow. In areas of increased blood flow, the intensity fluctuations of the speckle pattern are more rapid, and when integrated over the camera exposure time (typically 1 to 10 ms), the speckle pattern becomes blurred in these areas. By acquiring a raw image of the speckle pattern and quantifying the blurring of the speckles in the raw speckle image by measuring the spatial contrast of the intensity variations, spatial maps of relative blood flow can be obtained.

To quantify the blurring of the speckles, the speckle contrast k, defined as the standard deviation of time-integrated intensity $s_I$ divided by the mean time-integrated intensity $\langle I \rangle$, is computed as, $$k = \frac{s_I}{\langle I \rangle} = \frac{\sqrt{\frac{\sum_{i=1}^{N}(I_i - \langle I \rangle)^2}{N-1}}}{\langle I \rangle} \quad (1)$$

The time-integrated intensity measurements, $I_1, I_2, I_3, \ldots$, and $I_N$ where N is a positive integer, may be from a single location at different times, multiple locations at one time, or multiple locations at different times. However, the set of samples must result from the same process. For functional activation, the temporal window over which samples are collected must be significantly less than the duration of the functional activation induced change in perfusion; including too many temporal samples will result in the undesirable situation in which the samples represent different physiological states. For spatial sampling, the spatial window must not be significantly greater than the diameters of the blood vessels of interest. Within these temporal and spatial sampling window limits, samples collected over time at one location are equivalent to samples from multiple locations at one time if ergodicity is valid, which is typically a reasonable assumption. For the spatial sampling used in the algorithms to be discussed in the present disclosure, $N=w^2$.

```
{Step 1}
SumAc = R₁(Raw)
SqSumAc = R₁(Raw) · R₁(Raw)
for i = 2 to w do
    SumAc = SumAc + Rᵢ(Raw)
    SqSumAc = SqSumAc + Rᵢ(Raw) · Rᵢ(Raw)
end for
{Step 2}
R₁(Sum) = SumAc
R₁(SqSum) = SqSumAc
for i = w + 1 to m do
    SumAc = SumAc − Rᵢ₋w(Raw) + Rᵢ(Raw)
    SqSumAc = SqSumAc − Rᵢ₋w(Raw) · Rᵢ₋w(Raw) +
        Rᵢ(Raw) · Rᵢ(Raw)
    Rᵢ₋w+1(Sum) = SumAc
    Rᵢ₋w+1(SqSum) = SqSumAc
end for
{Step 3}
SumAc = C₁(Sum)
SqSumAc = C₁(SqSum)
for j = 2 to w do
    SumAc = SumAc + Cⱼ(Sum)
    SqSumAc = SqSumAc + Cⱼ(SqSum)
end for
{Step 4}
for j = w + 1 to n do
    B = SumAc
    SqB = SqSumAc
    SumAc = SumAc − Cⱼ₋w(Sum) + Cⱼ(Sum)
    SqSumAc = SqSumAc − Cⱼ₋w(SqSum) + Cⱼ(SqSum)
    Cⱼ₋w(Sum) = B
    Cⱼ₋w(SqSum) = SqB
end for
Cₙ₋w+1(Sum) = SumAc
Cₙ₋w+1(SqSum) = SqSumAc
{Step 5}
for i = 1 to m − w + 1 do
    for j = 1 to n − w + 1 do
```

$$K_{ij} = \frac{\sqrt{\frac{w^2 \times \text{SqSum}_{ij} - \text{Sum}_{ij}^2}{w^2 \times (w^2 - 1)}}}{\frac{\text{Sum}_{ij}}{w^2}}$$

```
    end for
end for
```

The roll method completely eliminates the redundant computations of the sums methods and performs rolling sums in two dimensions. Consequently, the roll method is an O(wmn) algorithm.

Though the above description of the roll method fully describes the efficiency of the approach in terms of arithmetic operation counts, it performs suboptimally on a modern computer. For maximal performance on a modern computer, as the vertical rolling sum is updated for a given pixel in a row, the horizontal rolling sum is computed for that pixel. This process occurs simultaneously for both the sum and square sum calculations. As soon as the sum and square sum are available for a given pixel, conversion to speckle contrast occurs. Thus, the data flows efficiently among the processor's registers, arithmetic logic units, floating point units, and other digital circuits with considerably less use of the cache and significantly less likelihood of needing to access main memory which can have disastrous effects on computation time. Although either the vertical or horizontal rolling sums may be computed first, performance is best when traversal of the array occurs in such a manner that memory locations are accessed contiguously. Implementing the roll method in this manner requires two 1-D arrays of integers with length equal to m, the width of the raw image. Memory for stack space is also required but will generally represent an insignificant amount of memory as is the case for the three previously described algorithms. Therefore, memory consumption is $O_m$.

In some embodiments, implementing the roll method in this manner may be superior to naively implementing the algorithm according to the description above because it uses the resources of a modern computer more efficiently; there is no difference in arithmetic operation counts. Fewer memory operations are necessary, and the amount of computational work between memory operations is greater making it more likely that the processor will be able to exploit the instruction level parallelism. Moreover, the long latencies in terms of processor cycles whenever memory is accessed and any limitations in memory bandwidth restrain the processor less. In addition, by using 1-D arrays instead of 2-D arrays, which would be required in a naive implementation of the roll method, the intermediate results are more likely to be accessible in the processor cache.

5. Vectorized Algorithm

In addition to the algorithms disclosed above, the present disclosure also provides for a parallel speckle contrast algorithm called the "vector" method for converting a raw image to a speckle contrast image.

Because the roll algorithm eliminates all arithmetic redundancy, algorithmic performance improvements are only possible via parallelism. The present disclosure provides parallelism for the roll method.

With the roll method, multiple raw images may be simultaneously processed, a raw image may be partitioned, the vertical rolling sums along the column vectors may be computed concurrently, the horizontal rolling sums along the row vectors may be processed in parallel, and may be evaluated simultaneously for different pixels. Each avenue for parallelism has caveats. Processing multiple raw images simultaneously introduces extra computations when averaging the speckle contrast images. Partitioning images requires overlap regions between the partitions which require extra calculations. Transitioning from parallel computation of the vertical rolling sums to parallel computation of the horizontal rolling sums is delayed by the necessary synchronization though the arithmetic operation burden is not greater than a nonparallel implementation of the roll algorithm. However, the present disclosure demonstrates that parallel processing via vector operations and multithreading lead to an additional performance improvement resulting in processing speeds close to 300 frames per second with standard computing hardware.

Vector operations or single instruction multiple data (SIMD) operations available on many modern processor architectures allow the simultaneous application of a given arithmetic operation on a vector of data as opposed to scalar data. Accordingly, the present disclosure also provides an implementation of the roll method using SIMD operations for the floating point calculations and to a lesser degree the integer computations. This implementation of the roll method is called the "vector" method.

6. Multithreaded Approaches

The SIMD operations used in the vector implementation may also employed in multithreaded approaches. The present disclosure also provides multithreaded approaches which are described in further detail below. In particular, the present disclosure provides three multithreaded approaches which are referred to herein as the mean threading method, the split method and the non-redundant method. In an ideal case, execution of a multithreaded algorithm with only one thread should require the same amount of time as the implementation entitled vector.

The simplest approach to parallelism via multithreading is to process distinct frames simultaneously to speed generation of an averaged laser speckle contrast image. This approach is referred to herein as the "mean" threading method. Fast image averaging is performed by accumulating a sum at each pixel after conversion of each raw image to a laser speckle contrast image. After processing all the images to be averaged, each pixel is divided by the image count. In the mean approach, fast image averaging can be used within the set of images dedicated to each thread, but after completion of each thread an additional averaging step is necessary among the sets of laser speckle contrast images derived from different threads. Also, the mean method will require t−1 additional 2-D arrays compared to the single-threaded implementation for storing the laser speckle contrast images for the threads prior to the final averaging step.

Another multithreaded algorithm is to divide the raw image into segments and process the segments simultaneously. In the present disclosure, this threading approach will be referred to as the "split" method, and the raw images will be split horizontally into equal numbers of adjacent rows. Because conversion of a raw image to a laser speckle contrast image results in a reduction of the horizontal and vertical dimensions, partitioning a raw image before processing will result in an image in which segments in the middle of the laser speckle contrast image are absent unless at the image division stage an overlap region between adjacent divisions is included. This method requires t−1 pairs of 1-D integer arrays of length equal to the raw image width beyond the memory requirements of the single-threaded case. The split method is an intermediate between the roll and sums algorithms. When one thread is used, the split method is identical to the roll algorithm. When (m−w+1)(n−w+1) threads, the maximum possible number of threads, are used with the necessary vertical and horizontal segmentation, the split method is equivalent to the sums algorithm.

The final multithreading method exploits the independence of the computations involving the vertical rolling sums among columns and the horizontal rolling sums among rows to avoid the redundant calculations inherent to the other two methods. In this method, which is called the "non-redundant" method, rather than processing one row at a time, t rows are divided into t sets of adjacent columns over which threads compute the vertical rolling sums on the shortened rows contained within each thread's assigned columns. Then, the horizontal rolling sums are computed for each of the t rows by one of the t threads. After using the sums and square sums to derive the speckle contrast at each pixel, the next t rows are processed by the same procedure until all rows in the raw image are processed. The non-redundant method needs two 2-D arrays of integers with dimensions of the raw image width by the number of threads rather than the two 1-D integer arrays of length equal to the raw image width as needed in the single-threaded case.

Although the non-redundant threading method has lower arithmetic operation counts as compared to the mean and split methods, deviation from the sequence of operations of the single-threaded standard C implementation and the frequent data synchronization requirements limit both the one and two threaded cases of the non-redundant method. Because the non-redundant method does not compute the horizontal sum of a row immediately following the vertical sum, less computational work is available between memory accesses.

B. Relative Correlation Time Algorithms

In some instances, it may be desirable to convert laser speckle contrast images to relative correlation time images, which have been found to be approximately proportional to perfusion. To convert a laser speckle contrast image to a relative correlation time image, speckle contrast is first converted to correlation time, which is a measure of the decay rate of the field autocorrelation. Then, the reciprocal of the correlation time is divided by the reciprocal of a baseline measure of correlation time that is derived from a different laser speckle contrast image. The ratio of the reciprocals of the correlation times for each pixel forms a relative correlation time image. The values in the relative correlation time image have been found to be approximately proportional to the relative change in perfusion though the relationship to absolute perfusion is not easily defined.

Equation 3 relates speckle contrast to correlation time where k is the speckle contrast, $\beta$ is a constant which accounts for speckle averaging but is often neglected, and x is the exposure duration of the camera divided by the correlation time.

$$k^2 = \beta \frac{\exp(-2x) - 1 + 2x}{2x^2}. \tag{3}$$

Since most experiments use a single exposure duration, computing the ratio of x from a given speckle contrast value to x from the baseline value is equivalent to the ratio of the reciprocals of the correlation times. Because the relationship between speckle contrast and correlation time is nonlinear, root-finding methods such as the Newton-Raphson method are often used. Since such root-finding methods impose a significant computational burden, simpler methods have also been explored.

As previously mentioned, the present disclosure provides relative correlation time algorithms for the conversion of a laser speckle contrast image to a relative correlation time image. Examples of suitable relative correlation time algorithms include, but are not limited to, the "Newton" method algorithm, the "table" method algorithm, the "hybrid" method algorithm, and the "asymptote" method algorithm. Each of these algorithms will be discussed in more detail below.

1. Newton Method Algorithm

All of the algorithms provided herein for converting a laser speckle contrast image to a relative correlation time image, except for one, are in some way dependent on a nonlinear root-finding method such as the Newton-Raphson method. Accordingly, the present disclosure provides what is referred to herein as the "Newton" method algorithm, which uses the Newton-Raphson method at each pixel of a laser speckle contrast image.

2. Table Method Algorithm

In another embodiment, the present disclosure provides the "table" method algorithm. This method generates a table which stores the ratios of camera exposure duration to correlation time indexed by speckle contrast values. By using the index within the table which is closest to the measured speckle contrast value, a measure of the correlation time will be obtained which has bounded error.

3. Hybrid Method Algorithm

In another embodiment, where the desired precision may necessitate the use of a table which would be prohibitively large, a "hybrid" method may be used which uses a relatively small table to generate good estimations for the Newton-Raphson method so that solution convergence occurs much faster. The hybrid method demonstrated in the Examples section of the present disclosure involves one table lookup and a single iteration of the Newton-Raphson method.

4. Asymptote Method Algorithm

In another embodiment, when the exposure duration is significantly greater than the correlation time, an asymptotic approximation may be used. When the asymptotic approximation is valid, the relationship between speckle contrast, k, and x, the camera's exposure duration divided by the correlation time is described by Equation 4. This approach is called the "asymptote" method.

$$x = \frac{1}{k^2}. \tag{4}$$

C. Processing Speeds and Other Considerations

As previously mentioned, the present disclosure provides methods of processing laser speckle contrast images at orders of magnitude greater speed than currently used algorithms. In some embodiments, laser speckle contrast images may be processed at a rate greater than or equal to 100 frames per second. In some embodiments, laser speckle contrast images may be processed at a rate greater than or equal to 200 frames per second. In some embodiments, laser speckle contrast images may be processed at a rate greater than or equal to 300 frames per second. As will be recognized by one of ordinary skill in the art with the benefit of this disclosure, the processing speed is dependent upon, among other things, computer speed.

In addition, in some embodiments, the methods of the present disclosure provide relative correlation time image processing at a rate greater than or equal to 200 frames per second. In some embodiments, the methods of the present disclosure provide relative correlation time image processing at a rate greater than or equal to 300 frames per second. In some embodiments, the methods of the present disclosure provide relative correlation time image processing at a rate greater than or equal to 400 frames per second. Again, as will be recognized by one of ordinary skill in the art with the benefit of this disclosure, the processing speed is dependent upon, among other things, computer speed. Consequently, the methods described in this disclosure may allow real-time processing of raw speckle images into relative correlation time images.

Generally, in all situations except when only a single speckle contrast value is needed, it may be desirable to utilize the roll method over the direct, sums, and FFT methods to obtain desirable performance results. In those embodiments when only a single speckle contrast value is needed, the sums method is recommended.

Furthermore, whenever possible, SIMD instructions and threading should be used. In most situations, the mean and split threading approaches will be about equally appropriate. Yet, when large amounts of image averaging is to be performed or when the window is very large the mean method will be preferable. Redundant calculations will prevent the mean and split threading methods from scaling well with high thread counts.

Generally speaking, when speckle contrast values are small, the asymptote method of speckle contrast to correlation time conversion may be preferable both for performance and accuracy reasons. Moreover, performance of the implementation could be further improved through use of SIMD instructions. The asymptote method is useful in more experiments than may be expected. In fact, $\beta$ has been successfully ignored in many previous biological studies because the effect of $\beta$ cancels when computing the relative correlation time when the asymptotic approximation is valid.

For speckle contrast values which are too large for accurate application of the asymptote method, the lookup table method is recommended. The presented range of speckle contrast error in cerebral blood flow imaging suggests that a table containing 3500 values should be sufficient to find the correlation time to within the uncertainty of the measurement in typical cerebral blood flow studies. Using a larger table as was done in the examples of this disclosure allows more accurate determination of the most likely correlation time within the distribution of probable correlation times for a given speckle contrast measurement. Generally, only experience will lead to knowledge about the range of expected speckle contrast values because the correlation time depends on the measured process rather than known quantities such as the coherence time of the laser. Furthermore, increasing exposure duration of the camera to ensure low speckle contrast values is ill advised not only because it will decrease temporal resolution but also because of the decrease in image contrast. Consequently, in certain embodiments, the implementation of both the asymptote and table methods are recommended and to select the appropriate method at computation time by the speckle contrast value. It is believed that this enables more accurate conversion than either method alone with performance generally between that of the asymptote and table methods. The computation time is less than that of the table method in many cases because table size can be reduced while maintaining the same accuracy, and the asymptote method is slightly faster whenever arithmetic performance is greater than memory speed. If additional precision is necessary, then the results of either the asymptote or table methods, whichever is applicable, should be used as a good initial guess for an iterative nonlinear equation solver as was done in the hybrid method.

Besides the obvious benefit of being able to observe the progress of experiments during the experiment, the roll algorithm and its parallel variants described in the present disclosure make it practical to work with large data sets. For measuring processes such as functional activation which have low signal-to-noise ratio, the algorithms described herein allow averaging of a greater number of experimental trials. When measuring a slow process such as cortical spreading depression, the algorithms described herein facilitate working with data sets with increased temporal resolution. Because it is possible for speckle contrast processing to occur more quickly than data acquisition in most experimental situations, processing time is rendered irrelevant if processing is performed during acquisition by the algorithms described herein. Implementations of the efficient algorithms described herein for processing of laser speckle contrast images and relative correlation time images are available for download.

To further illustrate various illustrative embodiments of the present disclosure, the following examples are provided.

EXAMPLES

Typical Cerebral Blood Flow Measurements

Figure 2A:
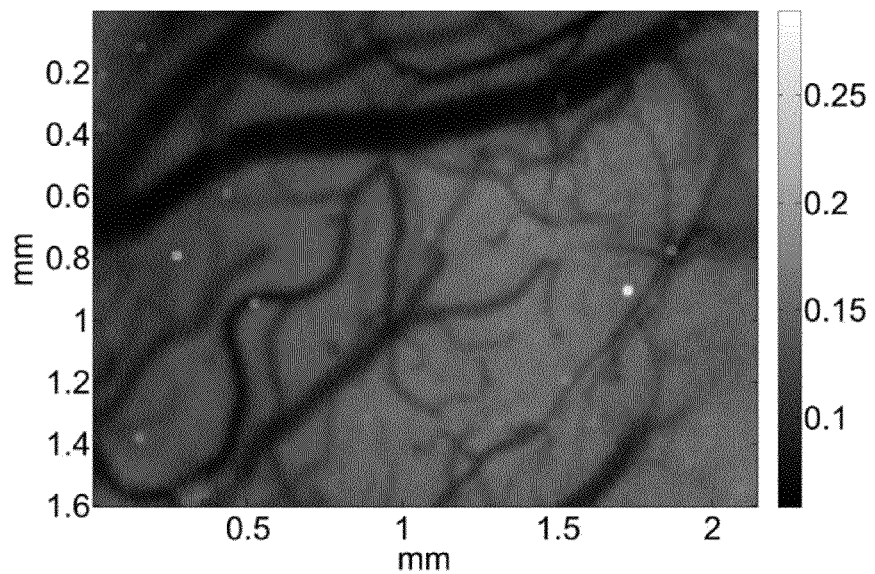
FIG. 2A depicts an example image of rat cerebral blood flow from 300 averaged laser speckle contrast images with windows of 7×7 pixels.

Typical results from rat cerebral blood flow studies were analyzed to discover the computational precision necessary to process images with fidelity. To expose the cerebral cortex, a craniotomy was performed on each experimental male Sprague-Dawley rat anesthetized with urethane (1.5 g/kg). All animal procedures were approved by the Animal Care and Use Committees of the University of Texas. The exposed portion of the cerebral cortex was illuminated with a 785-nm wavelength laser diode (Sanyo DL7140-201S). Images were captured with 5 ms exposures using an 8-bit CMOS camera (Basler A6020 operating at its maximum frame rate of 100 frames per second. FIG. 2A is a typical laser speckle contrast image of rat cerebral cortex. 300 raw images were processed using a 7×7 pixel window into 650×485 pixel laser speckle contrast images and were averaged. The blood vessels appear dark indicating a low speckle contrast value.

Figure 2B:
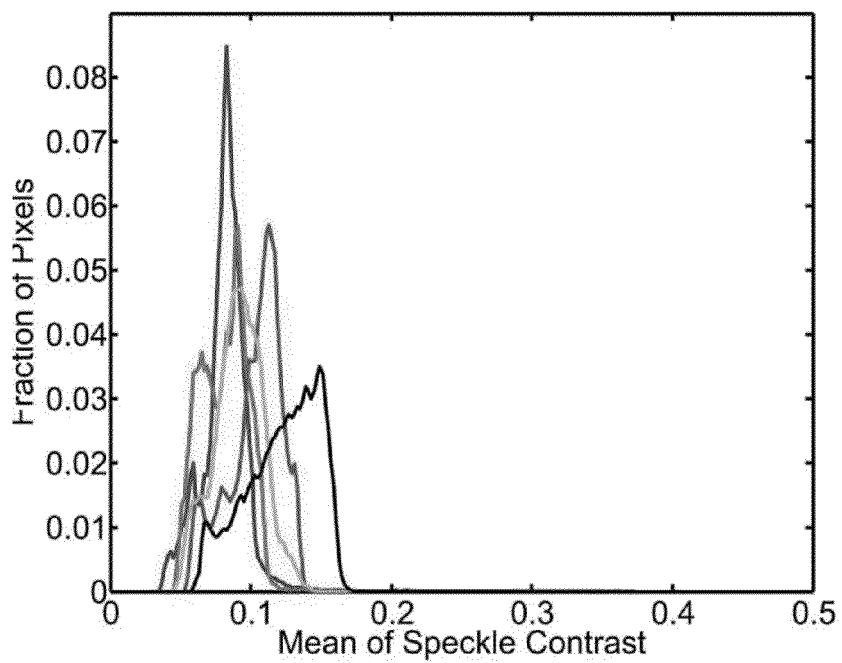
FIG. 2B is a graph containing five histograms of speckle contrast over the entire laser speckle contrast image from five experiments each with a different rat. The black distribution is from the image in FIG. 2A.

FIG. 2B shows the distributions of speckle contrast values from five distinct laser speckle contrast images produced from five different experiments using five different animals. Speckle contrast values were counted via placement into equally spaced bins with an interval of 0.002. As in FIG. 2A, 300 laser speckle contrast images were averaged. The black distribution is from the image in FIG. 2A. Most of the pixels have speckle contrast values below 0.15, and virtually no pixels have speckle contrasts above 0.2.

Figure 3A:
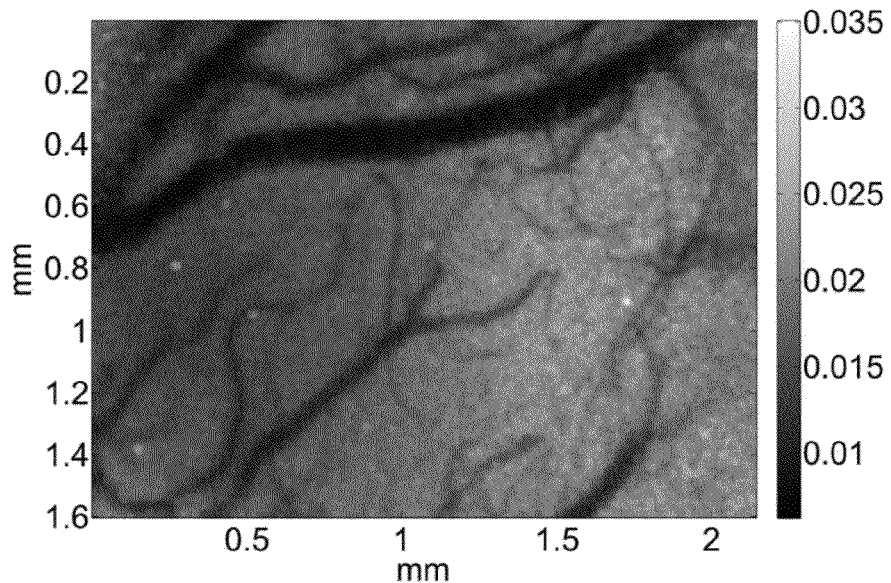
FIG. 3A depicts an image of the standard deviation of speckle contrast among the 300 laser speckle contrast images of FIG. 2A.

FIG. 3A is an image of the standard deviation of the speckle contrast values at a given pixel throughout the 300 laser speckle contrast images that contributed to the averaged laser speckle contrast image in FIG. 2A. Thus, FIG. 3A is an estimate of the uncertainty in the speckle contrast values of FIG. 2A. Generally, the areas representing the blood vessels have a lower standard deviation than the surrounding tissue indicating that the speckle contrast values from these regions are closer to converging to the true speckle contrast value than the surrounding tissue. This is expected because higher velocities have shorter correlation times which effectively leads to more independent samples of the process dynamics within a given exposure duration. With greater sampling, the variance is less, and the statistics converge faster.

Figure 3B:
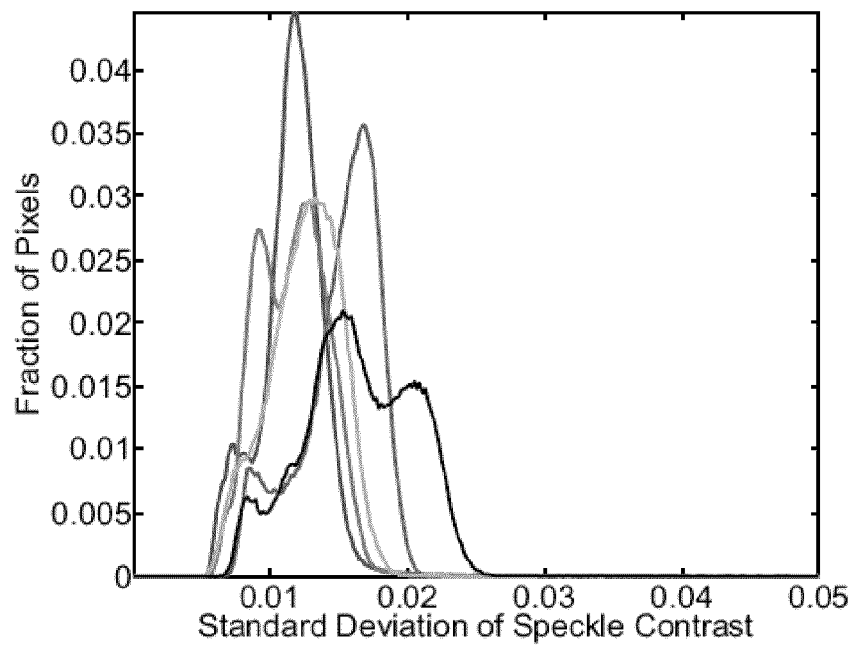
FIG. 3B is a graph containing histograms of the standard deviation of speckle contrast among 300 laser speckle contrast images for five laser speckle contrast image sets. The black distribution is from the image in FIG. 3A.

The distributions of the standard deviations of speckle contrast at a given pixel are presented in FIG. 3B. Equally spaced bins with an interval of 0.0002 were used. The distributions in FIG. 2B and FIG. 3B with the same color were generated from the same data. The five distributions show that the standard deviation may be as high as about 0.025 and as low as 0.005. Based on FIG. 2B and FIG. 3B, the speckle contrast values of a single laser speckle contrast image are only about one order of magnitude greater than the noise floor in cerebral blood flow studies. These results are comparable to the variations in speckle contrast during repeated electrical forepaw stimulation in rats. The vast majority of the noise is from variability in physiology. Because the signal-to-noise ratio is low, averaging of laser speckle contrast images is almost always performed. Using the smallest standard deviation from the five distributions leads to a standard error of 0.00029 when averaging 300 laser speckle contrast images. Consequently, 32-bit IEEE floating point numbers are sufficient to represent the speckle contrast values for these example measurements.

Performance Comparison of Algorithms

To evaluate the performance of the algorithms described in the present disclosure, the algorithms were written in the C programming language and were compiled using Microsoft Visual C++.NET 2003. The implementations were limited to the ISO C standard. The binaries were executed within Microsoft Windows XP SP2 on an Intel Pentium D operating at 3.2 GHz with 2 GB of dual channel 533 MHz DDR2 RAM. All FFTs were performed with FFTW version 3.1.2.

FIG. 4A shows the computation time required to process 10 raw images of 768×512 pixels while varying the square window from 2×2 to 128×128 pixels. FIG. 4A shows that the computation time of the direct and sums method initially increases quadratically as the window size increases. If the window size was incremented until it equaled the size of the image, the rate of increase would slow until reaching a maximum when the window size is half of the raw image dimensions. Then the computation time of the direct and sums algorithms would decrease producing a nearly symmetric performance curve. In FIG. 4A, the performance of the FFT and roll methods appears to be independent of window size. However, FIG. 4B which is a magnified version of FIG. 4A shows the gradual decrease in computation time as the window size is increased. The sums and roll method share the curve shape of the direct and FFT algorithms respectively but have lower overhead. The superior efficiency of the roll method is challenged only when the window consumes the entire raw image.

FIG. 5A and FIG. 5B address the impact of varying the height and width of raw images on computation time. The window size was fixed at 7×7 pixels, and either the width or height, whichever was not varied, was always 2048 pixels. Computation time represents processing of 10 frames. Only heights and widths which are powers of two are shown to reduce the complexity of analyzing the performance of the FFT algorithm. As shown, the direct, sums, and roll method have a linear relationship with image height and width. The FFT curves do not show much curvature despite the FFT having scaling.

Although linear scaling apparently dominates the performance curve for the FFT method, other problems arise when using this method with large images. Namely, with large images the inverse FFT has a tendency to overflow especially when small windows which have high spatial frequency bandwidths are used. For the other algorithms, overflow is only an issue when using impractically large windows. For overflow to even be possible, the window would have to exceed 181×181 pixels with 8-bit data with the implementations of the sums and roll algorithms of the present disclosure. Furthermore, the window size would have to be larger in order for overflow to be likely. Though criteria for overflow in the case of the direct method is not easily defined because of the combination of integer and floating-point operations, experience indicates that the direct method will at least scale to window sizes possible with the sums and roll methods.

The measurements presented in FIG. 4 and FIG. 5 combined with theoretical analysis lead to Equations 5-8 which describe the computation times per frame, $T_d$, $T_s$, $T_f$, and $T_r$, for the direct, sums, FFT, and roll algorithms, respectively, in terms of window size, raw image height, and raw image width. The nonnegative constants $k_{d1}$, $k_{d2}$, $k_{s1}$, $k_{s2}$, $k_{f1}$, $k_{f2}$, $k_{f3}$, $k_{f4}$, $k_{r1}$, $k_{r2}$ and $k_{r3}$ will depend on how quickly the algorithm implementation executes on a given computer. In other words, the nonnegative constants are determined by the speed of addition, multiplication, memory loads and stores, and other instructions in the sequence of the implementation. For the test case, $k_{d1}$, is 3.7 ns, $k_{d1}$ is 220 ns, $k_{s1}$ is 2.6 ns, $k_{s2}$ is 190 ns, $k_{f1}$ is 6.8 ns, $k_{f2}$ is 6.8 ns, $k_{f3}$ is 0 ns, $k_{f4}$ is 26 ns, $k_{r1}$ is 4.9 ns, $k_{r2}$ is 3.2 ns, and $k_{r3}$ is 18 ns as determined by linear least-squares fitting of the performance curves. The log(m) and log(n) in Equation 8 may be reduced somewhat with a more complicated overlap-add or overlap-save method of FFT-based convolution.

$$T_d = k_{d1} w^2 (m - w + 1)(n - w + 1) + k_{d2}(m - w + 1)(n - w + 1) \quad (5)$$

$$T_s = k_{s1} w^2 (m - w + 1)(n - w + 1) + k_{s2}(m - w + 1)(n - w + 1) \quad (6)$$

$$T_f = k_{f1} nm \log(m) + k_{f2} mn \log(n) + k_{f3} mn + k_{f4}(m - w + 1)(n - w + 1) \quad (7)$$

$$T_r = k_{r1} mn + k_{r2} mn + (n - w + 1) + k_{r2}(m - w + 1)(n - w + 1). \quad (8)$$

When setting height, width, and window size to values representative of an actual experimental setup, the roll method performs best followed by the FFT method as shown in FIG. 6. The direct method requires the most computation time. For the test, ten speckle contrast images were averaged. The raw image height was 512, and the width was 768. A window size of 7 pixels was used. The results represent the average computation time over 100 executions of each algorithm.

Parallel Speckle Contrast Algorithms

For the "vector" implementation of the roll method, we used Streaming SIMD Extensions (SSE) and Streaming SIMD Extensions 2 (SSE2) supported by processors produced by Advanced Micro Devices (AMD) and Intel because the ISO C standard does not include explicit support for SIMD operations.

FIG. 7 shows the significant performance improvement between the vector implementation and the standard roll method. Image parameters in FIG. 7 are the same as in FIG. 6. Almost the entire 34.6% improvement is due to acceleration of the floating point calculations in Equation 2. Little, if any, performance improvement is seen in vectorizing the integer operations because the processor used automatically identified and concurrently evaluated the integer operations which do not exhibit data dependence.

A version of square root precise to only 11 bit was used and is acceptable at least in the application of laser speckle contrast imaging to cerebral blood flow measurements as indicated in the sample data presented earlier. Optimization of square root evaluation resulted in the largest performance improvement attributable to a single operation. Of course, if there is interest only in the correlation time and not the speckle contrast, no square root is necessary.

Multithreaded Approaches

The SIMD operations used in the vector implementation were also employed in the three multithreaded approaches previously described, which are the mean threading method, the split method and the non-redundant method. Threading was implemented using the native threading functions of Microsoft Windows.

Single-threaded execution of the mean and split methods was nearly as fast as the vector implementation as seen in FIG. 7, but the overhead imposed by enabling threading was still observable. With the given height, width, and window size, the computation time reduction from increasing from one to two thread execution with the mean and split methods was 45.3% and 48.5%, respectively. In this example, the split method appeared faster because there are about $(t-1)(nw-1)/mf/t$ redundant integer additions per thread which required less time than about $(t-1)(n-w+1)/t$ redundant floating point additions per thread of the mean method. f represents the number of averaged laser speckle contrast images or frames.

In FIG. 7, the extra floating point additions of the mean method were more numerous than the extra integer additions of the split method and were individually more computationally expensive than an integer addition though only marginally so due to efficient use of SIMD instructions.

The non-redundant method does not compute the horizontal sum of a row immediately following the vertical sum, and accordingly, less computational work is available between memory accesses. This explains the increase in computation time as compared to the vector implementation observable in FIG. 7. Moreover, burden imposed by the large amount of processor core communication for data synchronization limits the improvement from one to two threaded execution to 37.5% rather than the idealized 50%. Though the non-redundant method performed poorly here, it will be the algorithm of choice for highly multithreaded processor architectures such as a graphics processing unit. In such architectures, instruction level parallelism matters less, while reduction of redundancy is very important for good performance.

Relative Correlation Time Algorithms

As previously mentioned, the present disclosure provides four algorithms for conversion of a laser speckle contrast image to a relative correlation time image. These algorithms are referred to herein as the Newton method, the table method, the hybrid method, and the asymptote method.

FIG. 8 shows the time required to convert laser speckle contrast images to relative correlation time images. The values represent time required to convert a single speckle contrast image with dimensions 762×506 which are the dimensions of speckle contrast images produced in the tests represented by FIGS. 6 and 7. Each speckle contrast value was a randomly selected value between zero and one, the minimum and maximum theoretical speckle contrast values respectively. Each algorithm was executed in such a way as to give accuracy levels which were as equivalent as possible. A table containing 16384 values was used for the table method, while the hybrid method used 8192 values. The Newton method is about 100 times slower than the table and asymptote method while being about 10 times slower than the hybrid method. Also, FIG. 8 shows the thread scaling of each algorithm. When converting speckle contrast to correlation time, the pixels exhibit complete independence and share no calculations unlike the case for generation of speckle contrast images. Thus, processing relative correlation time images is readily parallelized and doubling the number of threads should nearly halve the computation time which is seen with the Newton and the hybrid methods. The table and asymptote methods deviate from this expected behavior because the computation time is so short that the thread initialization time imposed by the operating system is significant.

In FIG. 9, the effect of varying the table size on computation time of the table method is shown. 4096×4096 sized images were used to minimize the thread scaling impact of the operating system's thread initialization time. Since the speckle contrast values are randomly selected, temporal and spatial locality optimizations in the processor cache and data prefetching are largely futile. Hence, the processor cache is effective only when the entire table fits within the cache. When the table is too large to fit within the cache, performance is limited by the latency and bandwidth of the processor's memory system. Each processor core of the Intel Pentium D used in this paper has a two megabyte L2 cache. Each entry in the lookup table consumes 4 bytes. With real images, the values of neighboring pixels will likely be close and hence temporal and spatial locality within the lookup table will be exploitable. Furthermore, the error measurements from above indicate that actual data does not span the entire interval between zero and one as suggested by theory.

With real data, the effective table size is the portion of the table actually accessed. Thus, with the data presented in the error measurements section the effective table size will be approximately a fifth of the actual size. Consequently, the results for the table method in FIGS. 8 and 9 represent worst case scenarios.

Because the memory system of each processor core is not independent, thread scaling deviates from ideal for large table sizes as seen in FIG. 9. Thread scaling is nearly ideal for small tables which fit within the L2 cache because each processor core of the Intel Pentium D used in this paper has its own L2 cache. Large table thread scaling is affected because both processor cores share the bus to main memory, and hence the latency and bandwidth issues when accessing main memory are exacerbated.

FIG. 10 shows the fractional error in determining the ratio of exposure duration to correlation time with the table and asymptote methods as a function of speckle contrast. Fractional error is the absolute value of the difference between the true value and the estimate value divided by the true value. Because generation of relative correlation time images involves ratios of x, fractional error is the best manner to quantify the significance of the deviation from the true value. The Newton-Raphson method was used to determine the true value of x. Clearly, for the asymptote method the deviation from the true value is unacceptable for high values of speckle contrast. However, with real data as shown in the sample experimental data the speckle contrast values are low. Thus, when there is caution, the asymptote method may be used.

Also shown in FIG. 10 is the maximum fractional error of the table method with table sizes of 1024, 4096, and 16384 values. Because the implementation of the table method in this paper chooses the index which is closest but not greater than the measured speckle contrast value, the error increases until the measured speckle contrast value becomes equal to the value of the next index. Therefore, the fractional error but not the maximum fractional error of the table method is a form of sawtooth wave with the minimum being zero. The maximum fractional error is the function which connects all of the peaks of the sawtooth wave. For a speckle contrast value k with $k_n \leq k < k_{n+1}$ where $k_n$ and $k_{n+1}$ are consecutive table indices, the maximum fractional error in x given k is $x_n/x_n+1-1$ where $x_n$ and $x_{n+1}$ are the values indexed by $k_n$ and $k_{n+1}$ respectively. In FIG. 10 the maximum fractional error curve decreases as the table size increases or equivalently the interval between speckle contrast value indices decreases. Unfortunately, the fractional error of the table method increases significantly for very small and large speckle contrast values because the ratio of exposure duration to correlation time in Equation 3 rapidly ascends to infinity for speckle contrast values that approach zero and rapidly descends to zero speckle contrast values that approach one. Though the maximum fractional error curve is determined by the table size, the magnitude of the fractional error as the speckle contrast value approaches zero or one is affected little by table size.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

REFERENCES

1. J. D. Briers and A. F. Fercher, "Retinal blood-flow visualization by means of laser speckle photography," *Invest. Ophthalmol. Vis. Sci., vol.* 22, pp. 255-259, 1982.
2. A. K. Dunn, H. Bolay, M. A. Moskowitz, and D. A. Boas, "Dynamic imaging of cerebral blood flow using laser speckle," *J. Cereb. Blood Flow Metab., vol.* 21, pp. 195-201, 2001.
3. C. Ayata, A. K. Dunn, Y. Gursoy-Ozdemir, Z. Huang, D. A. Boas, and M. A. Moskowitz, "Laser speckle flowmetry for the study of cerebrovascular physiology in normal and ischemic mouse cortex," *J. Cereb. Blood Flow Metab., vol.* 24, pp. 744-755, 2004.
4. H. K. Shin, A. K. Dunn, P. B. Jones, D. A. Boas, M. A. Moskowitz, and C. Ayata, "Vasoconstrictive neurovascular coupling during focal ischemic depolarizations," *J. Cereb. Blood Flow Metab.*, vol. 26, pp. 1018-1030, 2006.
5. A. J. Strong, E. L. Bezzina, P. J. B. Anderson, M. G. Boutelle, S. E. Hopwood, and A. K. Dunn, "Evaluation of laser speckle flowmetry for imaging cortical perfusion in experimental stroke studies: Quantitation of perfusion and detection of peri-infarct depolarisations," *J. Cereb. Blood Flow Metab., vol.* 26, pp. 645-653, 2006.
6. A. J. Strong, P. J. Anderson, H. R. Watts, D. J. Virley, A. Lloyd, E. A. Irving, T. Nagafuji, M. Ninomiya, H. Nakamura, A. K. Dunn, and R. Graf, "Peri-infarct depolarizations lead to loss of perfusion in ischaemic gyrencephalic cerebral cortex," *Brain*, vol. 130, no. 4, pp. 995-1008, 2007.
7. T. M. Le, J. S. Paul, H. Al-Nashash, A. Tan, A. R. Luft, F. S. Sheu, and S. H. Ong, "New insights into image processing of cortical blood flow monitors using laser speckle imaging," *IEEE Trans. Med. Imag.*, vol. 26, no. 6, pp. 833-842, June 2007.
8. K. R. Forrester, C. Stewart, J. Tulip, C. Leonard, and R. C. Bray, "Comparison of laser speckle and laser doppler perfusion imaging: Measurement in human skin and rabbit articular tissue," *Med. Biol. Eng. Comput.*, vol. 40, pp. 687-697, 2002.
9. X. W. He and J. D. Briers, "Laser speckle contrast analysis (LASCA): A real-time solution for monitoring capillary blood flow and velocity," *Proc. SPIE*, vol. 3337, pp. 98-107, 1998.
10. J. D. Briers and X. W. He, "Laser speckle contrast analysis (LASCA) for blood flow visualization: Improved image processing," *Proc. SPIE*, vol. 3252, pp. 26-33, 1998.
11. J. D. Briers, "Laser doppler, speckle and related techniques for blood perfusion mapping and imaging," *Physiol. Meas.*, vol. 22, pp. R35-R66, 2001.
12. R. Bandyopadhyay, A. S. Gittings, S. S. Suh, P. K. Dixon, and D. J. Durian, "Speckle-visibility spectroscopy: A tool to study time-varying dynamics," *Rev. Sci. Instrum.*, vol. 76, pp. 093110-093110, 2005.
13. H. Cheng and T. Q. Duong, "Simplified laser-speckle-imaging analysis method and its application to retinal blood flow imaging," *Opt. Lett.*, vol. 32, no. 15, pp. 2188-2190, August 2007.
14. S. Yuan, A. Devor, D. A. Boas, and A. K. Dunn, "Determination of optimal exposure time for imaging of blood flow changes with laser speckle contrast imaging," *Appl. Opt.*, vol. 44, no. 10, pp. 1823-1830, April 2005.
15. T. F. Chan and J. G. Lewis, "Computing standard deviations: Accuracy," *Comm. ACM*, vol. 22, no. 9, pp. 526-531, September 1979.

What is claimed is:

1. A method comprising:
   obtaining a raw speckle image of a sample;
   converting the raw speckle image to a laser speckle contrast image using a laser speckle contrast algorithm; and
   converting the laser speckle contrast image to a relative correlation time image using a relative correlation time algorithm;
   wherein the laser speckle contrast algorithm is a direct algorithm that uses the following formula:

$$k = \frac{s_I}{\langle I \rangle} = \frac{\sqrt{\frac{\sum_{i=1}^{N}(I_i - \langle I \rangle)^2}{N-1}}}{\langle I \rangle}$$

where speckle contrast k is equal to the standard deviation of time-integrated intensity $s_I$ divided by the mean time-integrated intensity $\langle I \rangle$ and where N is a positive integer.

2. A method comprising:
   obtaining a raw speckle image of a sample;
   converting the raw speckle image to a laser speckle contrast image using a laser speckle contrast algorithm; and
   converting the laser speckle contrast image to a relative correlation time image using a relative correlation time algorithm;
   wherein the laser speckle contrast algorithm is a sums algorithm that uses the following formula:

$$k = \frac{s_I}{\langle I \rangle} = \frac{\sqrt{\dfrac{N\sum_{i=1}^{N} I_i^2 - \left(\sum_{i=1}^{N} I_i\right)^2}{N(N-1)}}}{\dfrac{\sum_{i=1}^{N} I_i}{N}}$$

where speckle contrast k is seen to be equal to the standard deviation of time-integrated intensity $s_I$ divided by the mean time-integrated intensity (I) and where N is a positive integer.

3. A method comprising:
obtaining a raw speckle image of a sample;
converting the raw speckle image to a laser speckle contrast image using a laser speckle contrast algorithm; and
converting the laser speckle contrast image to a relative correlation time image using a relative correlation time algorithm;
wherein the laser speckle contrast algorithm is a fast Fourier transform-based convolution algorithm that uses the following formula:

$$k = \frac{s_I}{\langle I \rangle} = \frac{\sqrt{\dfrac{\sum_{i=1}^{N}(I_i - \langle I \rangle)^2}{N-1}}}{\langle I \rangle}$$

where speckle contrast k is seen to be equal to the standard deviation of time-integrated intensity $s_I$ divided by the mean time-integrated intensity (I) and where N is a positive integer.

4. A method comprising:
obtaining a raw speckle image of a sample;
converting the raw speckle image to a laser speckle contrast image using a laser speckle contrast algorithm; and
converting the laser speckle contrast image to a relative correlation time image using a relative correlation time algorithm;
wherein the laser speckle contrast algorithm is a roll algorithm that uses the following formula:

$$k = \frac{s_I}{\langle I \rangle} = \frac{\sqrt{\dfrac{N\sum_{i=1}^{N} I_i^2 - \left(\sum_{i=1}^{N} I_i\right)^2}{N(N-1)}}}{\dfrac{\sum_{i=1}^{N} I_i}{N}}$$

where speckle contrast k is seen to be equal to the standard deviation of time-integrated intensity $s_I$ divided by the mean time-integrated intensity (I) and where N is a positive integer.

5. A method comprising:
obtaining a raw speckle image of a sample;
converting the raw speckle image to a laser speckle contrast image using a roll algorithm that uses the following formula:

$$k = \frac{s_I}{\langle I \rangle} = \frac{\sqrt{\dfrac{N\sum_{i=1}^{N} I_i^2 - \left(\sum_{i=1}^{N} I_i\right)^2}{N(N-1)}}}{\dfrac{\sum_{i=1}^{N} I_i}{N}}$$

where speckle contrast k is seen to be equal to the standard deviation of time-integrated intensity $s_I$ divided by the mean time-integrated intensity (I) and where N is a positive integer; and
converting the laser speckle contrast image to a relative correlation time image using a relative correlation time algorithm.

6. The method of claim 5 wherein the relative correlation time algorithm is a Newton method algorithm, a table method algorithm, a hybrid method algorithm, or an asymptote method algorithm.

7. The method of claim 5 wherein converting the raw speckle image to a laser speckle contrast image occurs at a rate greater than or equal to 100 images per second.

8. The method of claim 5 wherein converting the laser speckle contrast image to the relative correlation time image occurs at a rate greater than or equal to 200 images per second.

* * * * *